United States Patent [19]

Töke et al.

[11] 4,229,366

[45] Oct. 21, 1980

[54] PROCESS FOR HETEROGENEOUS NUCLEOPHILIC SUBSTITUTION REACTIONS

[75] Inventors: László Töke; Gabor T. Szabo; Gábor Szabó, all of Budapest; Lajos Nagy, Szentendre; Istvan Rusznák, Budapest, all of Hungary

[73] Assignee: Chinoin Gyógyszer és Vegyészeti Terméker Gyára Rt., Budapest, Hungary

[21] Appl. No.: 953,164

[22] Filed: Oct. 20, 1978

[30] Foreign Application Priority Data

Oct. 20, 1977 [HU] Hungary ............................... CI 1779

[51] Int. Cl.² ..................... C07C 69/14; C07C 120/04
[52] U.S. Cl. ............................ 260/465 F; 260/465 R; 560/236; 560/254
[58] Field of Search ........... 260/465 R, 465 F, 465 G; 560/236, 254

[56] References Cited

U.S. PATENT DOCUMENTS

| | | | |
|---|---|---|---|
| 3,413,309 | 11/1968 | Makosza et al. | 260/465 F X |
| 3,839,399 | 10/1974 | Starks et al. | 260/465 R |
| 3,992,432 | 11/1976 | Napier et al. | 260/465.1 |
| 4,056,509 | 11/1977 | Verbrugge et al. | 260/465 R |
| 4,118,413 | 10/1978 | Wood | 260/465 D |

OTHER PUBLICATIONS

Cook et al., Chemical Abstracts, vol. 82, 3700g (1975).
Zubrick et al., Chemical Abstracts, vol. 82, 154561p (1975).

*Primary Examiner*—Dolph H. Torrence
*Attorney, Agent, or Firm*—Karl F. Ross

[57] ABSTRACT

The invention relates to a process for nucleophilic substitution reactions. According to the invention the reaction is carried out in a heterogeneous system, consisting of a solid and a dissolved reactant, one or several organic solvents, one or several linear polyether derivatives, and/or amino compounds and water.

The volume of the water is preferably at the most 100% of the volume of the organic solvent and more preferably 5%.

According to the invention the anhydrous reaction medium which is difficult to ensure, is not necessary and the use of the expensive and in industrial scales unavailable crown ethers is eliminated.

11 Claims, No Drawings

PROCESS FOR HETEROGENEOUS NUCLEOPHILIC SUBSTITUTION REACTIONS

The present invention is related to a process for nucleophilic reactions.

According to the invention the reaction is carried out in a heterogeneous system containing one reactant in the solid state, the other in a dissolved state and the reaction mixture contains one or several organic solvents, one or several linear polyether derivatives and/or amino compounds and water.

In the course of the process of the invention, preferably water-inmiscible solvents, such as aromatic, and aliphatic hydrocarbons, particularly benzene and homologues thereof may be used as organic solvents. Other solvents, which are stable under the reaction conditions and dissolve one component of the system, may also be employed.

As linear polyether derivatives preferably such polyether derivatives are used, which consist of lower alkylene and oxygen units, such as polymerizates of lower glycols, such as polyethylene glycol.

As amino compounds preferably tri(lower)alkyl amines, such as triethylamine, may be employed.

The reaction may be carried out in the presence of linear polyether derivatives only, amino compounds only or in the presence of both. The reaction may also be performed in the presence of amino compounds, which may be prepared by replacing the terminal hydroxy group of linear polyether derivatives by a secondary amino group. The latter compounds may contain a di(lower alkyl)amino or a cyclic amino group, such as a 1-piperidyl group as a terminal amino group.

The amount of water that may be in the reaction mixture is varied within a wide range. The water content is preferably about 0.5 to 50% calculated relative to organic solvents therein.

Lower alkyl stands for an alkyl group containing 1 to 4 carbon atoms.

In the nucleophilic substitution reactions carried out with anions, the anion is preferably used in the form of a salt thereof. The alkali salts do not dissolve or dissolve poorly, in organic solvents.

Such reactions are typically carried out in a heterogeneous system. The alkali salt or hydroxide is used in an aqueous medium and the other reactant is used in an organic solvent solution.

The substance transport between the layers is a critical factor of the process. The transport was originally promoted by increasing the dispersity, by using emulsifying agents.

In 1951 (C. R. Acad. Sci., Ser. C. 232, 1424 (1951) the phase transfer catalytic effect of quaternary ammonium salts was recognized. In 1965 generally suitable methods were elaborated (Dutch Patent Applicatiion No. 6,412,937) and the phenomenon has been explained from a theoretical point of view as well (J. A. C. S. 93, 195 (1971). With the aid of the above results the salt in aqueous solution could be readily reacted with the substrate.

For industrial purposes however, processes, wherein the salt need not be previously dissolved, are more preferable.

It has been reported that the outstanding complex forming capability of crown ethers with alkali ions may be used for activation of the anion accompanying these ions (J. A. C. S. 89, 7017 (1967).

This phenomenon is used for conducting the reactions of the alkali salts by dissolving the substrate and the crown ether in an organic solvent and by moving the salt in the reaction mixture by a stirrer as a dispersion. For a similar purpose cryptates, phosphoric acid amides and some polyamino compounds may be used as well (Synth. 1975, 805).

The price of the above compounds is very high, and the use thereof requires an anhydrous medium.

We have surprisingly found, that these compounds containing polyether chains of different length show an outstanding catalytic activity if apart from the solid and organic layers there is a small amount of water present as well. This occurred in the case of some amines too.

This type of cocatalysis is a new method for realization of phase-transfer reactions and thus a similar or a better effect could be achieved than that obtained with crown ethers, when using the otherwise weak polyethylene glycol catalyst. Thus polyethylene glycol may be used in preparative laboratory or industrial practice, as the reaction and the processing of the reaction mixture is very simple, and the costs of the catalyst are much lower than the costs of the catalysts used so far.

A further advantage of the process according to the invention is the fact that an excess of alkali-, alkali earth metal- or ammonium salts or hydroxides is not necessary or a smaller amount of excess is necessary than in the case of the known processes.

As the process of the invention is suitable for different nucleophilic reactions, by chosing the best reactants the process of the invention may be used in the field of the preparative organic chemical practice and in the big field of industry. The following examples are mentioned as suitable nucleophilic reactants without limiting the invention to these reactants: alkali or alkali earth metal hydroxides, halides, sulfides, hydrogen sulfides, phenolates, enolates, cyanides, rhodanides, cyanates, nitrates, azides, cyanamides, carboxylates, sulfonates, but organic compounds containing loosened carbon-hydrogen bond and mercaptane salts may also be used. As a substrate - another reactant of the reaction - all compounds suitable for nucleophilic reactions - may be employed. Such compounds without limiting the scope of the invention to these compounds, are compounds containing carbon-halogen bond, such as unsubstituted and substituted benzyl halides.

The further details of the invention are illustrated by the following examples without limiting the scope of the invention to the examples.

EXAMPLE 1

To a 25 ml. flask equipped with a stirrer and reflux 10 ml. of benzene, 0.15 g. of polyethylene glycol of average molecular weight of 300, 3.25 g. (0.05 mole) of potassium cyanide and 0.5 ml. of water are added. The reaction mixture is gently boiled under stirring and under reflux for 15 minutes whereafter 5.7 ml. (0.05 mole) of benzyl chloride are added and the reaction mixture is further boiled under stirring and reflux.

The reaction is followed by gas chromatography. The conversion is completed in 4.5 hours.

The reaction mixture is then cooled, filtered and the precipitate is washed with benzene. The combined benzene filtrates are dried with magnesium sulphate and the benzene is removed by distillation and the residue is distilled.

The main cut is collected at 15 torr at a temperature of 105° to 120° C. Yield: 4.69 g. (80.2%) of benzyl cyanide.

EXAMPLE 2

To a 100 ml. flask equipped with a stirrer and reflux 50 ml. of toluene, 0.75 g. of polyethylene glycol of average molecular weight of 300, 0.5 ml. of water, 0.5 ml. of triethylamine and 24.5 g. (0.25 mole) of potassium acetate are introduced. The reaction mixture is maintained at 100° C. under stirring for 15 minutes and 28.5 ml. (0.25 mole) of benzyl chloride are added whereafter the mixture is further heated for 3.5 hours at 100° C. under steady stirring.

The reaction mixture is cooled, filtered and the precipitate is washed with toluene and the combined toluene filtrates are dried with sodium sulphate, the toluene is distilled off and the residue is distilled at atmospheric pressure. The main cut is collected at 210°–225° C.

Yield 29.96 g. (80.5%) of benzyl acetate.

EXAMPLE 3

The process of Example 1 is used but instead of polyethylene glycol of average molecular weight of 300 a polyether in the same amount is used which was prepared from polyethylene glycol of an average molecular weight of 300 by conversion of the terminal group into a 1-piperidyl group. According to gas chromatographic analysis the conversion is completed within 4 hours.

Yield: 4.96 g. (85%) of benzyl cyanide.

EXAMPLE 4

The process of Example 1 is used but instead of the polyethylene glycol of molecular weight 300, 0.10 g. of triethylamine is used as a catalyst. According to gas chromatographic analysis the conversion is completed within 4.5 hours.

Yield: 4.66 g. (80%) of benzyl cyanide.

EXAMPLE 5

To a 250 ml. flask equipped with a stirrer and reflux 40 ml. of benzene, 0.5 g. of polyether of a molecular weight of 300 containing 1-piperidyl terminal group, 2 ml. of water and 9.8 g. (0.15 mole) of potassium cyanide are introduced. The reaction mixture is gently boiled whereafter 28.4 g. (0.15 mole) of 3,4-dimethoxy-benzylchloride are added.

The reaction mixture is stirred for 3.5 hours under mild heating. The conversion is substantially completed.

The mixture is cooled, filtered and the precipitate is washed with benzene. The combined benzene filtrates are dried with magnesium sulphate and benzene is distilled off and the residue is distilled. The main cut is collected at 15 torr and at 190°–200° C.

Yield: 20.0 g. (75%) of 3,4-dimethoxy-benzyl cyanide.

EXAMPLE 6

The process of Example 5 is used but instead of polyethylene glycol having a 1-piperidyl terminal group of an average molecular weight of 300, polyethylene glycol of an average molecular weight of 300 is used, in the same amount.

The conversion is substantially completed within 3.5 hours. Yield: 19.8 g. (74%) of 3,4-dimethoxy-benzyl cyanide.

EXAMPLE 7

The process of Example 5 is used but as a starting material instead of the purified 3,4-dimethoxy-benzyl chloride, 39.1 g. of the residue is used which is obtained by evaporation of the reaction mixture serving for the preparation of 3,4-dimethoxy-benzyl chloride, containing 28.4 g. of 3,4-dimethoxy-benzyl chloride.

Yield: 20.2 g. (76%) of 3,4-dimethoxy-benzyl cyanide.

EXAMPLE 8

To a 250 ml. flask equipped with a stirrer and reflux 20 ml. of benzene, 0.5 g. polyether having a 1-piperidyl terminal group of an average molecular weight of 300, 0.5 ml. of triethylamine, 7.35 g. (0.15 moles) of sodium cyanide and 10 ml. of water are introduced. The reaction mixture is gently heated under reflux for 15 minutes, whereafter 145 g. of 19.6% 3,4-dimethoxy-benzyl chloride in benzene are added. (3,4-dimethoxy-benzyl chloride content: 0.15 moles).

The reaction mixture is heated for 3.5 hours under stirring and reflux. The conversion is completed.

The mixture is cooled, the aqueous layer is separated; and the organic layer is washed twice with 20 ml. of water. The benzene solution is dried with magnesium sulphate, evaporated and the residue is fractionated in vacuo.

The main cut is collected at 190°–200° C. Yield: 19.5 g. (73.4%) of 3,4-dimethoxy-benzyl cyanide.

What we claim is:

1. A process for carrying out a nucleophilic substitution reaction which comprises the step of conducting the reaction in a heterogeneous system containing a nucleophilic reagent selected from the group consisting of alkali metal, alkali earth metal or ammonium cyanides and carboxylates and a benzyl halide substrate wherein one of said nucleophilic reagent and said benzyl halide substrate is in a solid state and the other is in a dissolved state, a water-immiscible solvent, water, and a phase transfer agent selected from the group consisting of a polymerizate of a lower alkylene glycol, a polymerizate of a lower alkylene glycol with a dilower alkylamine group or 1-piperidyl group terminally substituted thereon, a mixture of a polymerizate of a lower alkylene glycol and a triloweralkyl amine, and mixtures thereof.

2. The process defined in claim 1 which comprises conducting the reaction wherein the volume of water is at most 100% of the volume of the water immiscible solvent.

3. The process defined in claim 2 wherein the volume of water is 5% of the volume of the water immiscible solvent.

4. The process defined in claim 1 wherein the phase transfer agent is a polyethylene glycol.

5. The process defined in claim 1 wherein the water immiscible solvent is benzene or toluene.

6. The process defined in claim 1 wherein the phase transfer agent is a polyethylene glycol having a piperidyl terminal group.

7. The process defined in claim 1 wherein the phase transfer agent is a mixture of a linear lower alkylene glycol and a trilower alkyl amine.

8. The process defined in claim 7 wherein the phase transfer agent is a mixture of a pulyethylene glycol having a piperidyl terminal group and triethylamine.

9. The process defined in claim 1 wherein the nucleophilic reactant is an alkali cyanide.

10. The process defined in claim 1 wherein the nucleophilic reactant is an alkali acetate.

11. The process defined in claim 1 wherein the benzyl halide is substituted by a methoxy group.

* * * * *